(12) United States Patent
Kampas et al.

(10) Patent No.: US 10,130,496 B2
(45) Date of Patent: Nov. 20, 2018

(54) ANKLE BRACE

(71) Applicant: OTTO BOCK HEALTHCARE PRODUCTS GMBH, Vienna (AT)

(72) Inventors: Philipp Kampas, Vienna (AT); Martin Seyr, Vienna (AT); Markus Schneegans, Rollshausen (DE); Roger Rost, Gottingen (DE); Stephan Lintner, Elsbethen (AT); Sebastian Kulessa, Bovenden (DE); Martin Mitterer, Bad Reichenhall (DE); Bernhard Van Mazijk, Riederberg (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 15/111,754

(22) PCT Filed: Jan. 8, 2015

(86) PCT No.: PCT/EP2015/000015
§ 371 (c)(1),
(2) Date: Jul. 14, 2016

(87) PCT Pub. No.: WO2015/106956
PCT Pub. Date: Jul. 23, 2015

(65) Prior Publication Data
US 2016/0331558 A1    Nov. 17, 2016

(30) Foreign Application Priority Data
Jan. 17, 2014 (DE) .................. 10 2014 000 647

(51) Int. Cl.
*A61F 2/66* (2006.01)
*A61F 2/50* (2006.01)
*A61F 2/76* (2006.01)

(52) U.S. Cl.
CPC ............ *A61F 2/6607* (2013.01); *A61F 2/50* (2013.01); *A61F 2/76* (2013.01); *A61F 2/66* (2013.01);
(Continued)

(58) Field of Classification Search
CPC ..................... A61F 2/66; A61F 2002/5001
See application file for complete search history.

(56) References Cited

U.S. PATENT DOCUMENTS

D354,567 S   *  1/1995  Forsthoff .................. D24/155
5,593,453 A      1/1997  Ahlert
(Continued)

FOREIGN PATENT DOCUMENTS

DE        813191 C     9/1951
DE        2130168 A1   1/1973
(Continued)

OTHER PUBLICATIONS

PCT International Search Report for PCT International Patent Application No. PCT/EP2015/000015, dated Apr. 1, 2015.

*Primary Examiner* — Bruce E Snow
(74) *Attorney, Agent, or Firm* — Holland & Hart (57) ABSTRACT

An ankle brace for a prosthetic device includes a prosthetic foot and a lower leg piece. The ankle brace may bridge a gap between the prosthetic foot and the lower leg piece. The ankle brace may include a main member which is made of a flexible material and includes a cavity for accommodating the prosthetic device. At least one reinforcement element may be arranged on the main member which may increase the inherent stability of the ankle brace.

20 Claims, 7 Drawing Sheets

(52) U.S. Cl.
CPC ............... *A61F 2002/5001* (2013.01); *A61F 2002/5007* (2013.01); *A61F 2002/5038* (2013.01); *A61F 2002/6614* (2013.01)

(56) References Cited

U.S. PATENT DOCUMENTS

| | | |
|---|---|---|
| 5,755,812 A | 5/1998 | Becker et al. |
| 5,778,563 A * | 7/1998 | Ahlbaumer ............. A43B 5/00 36/140 |
| 6,592,539 B1 | 7/2003 | Einarsson et al. |
| 6,911,049 B2 | 6/2005 | Laghi |
| 2002/0077703 A1 | 6/2002 | Johnson et al. |
| 2005/0197611 A1 * | 9/2005 | Taranow ................. A61F 5/01 602/62 |
| 2006/0015192 A1 | 1/2006 | Clausen et al. |
| 2012/0283846 A1 | 11/2012 | Janssen et al. |
| 2013/0326799 A1 | 12/2013 | Bue, Jr. et al. |
| 2015/0351934 A1 | 12/2015 | Sawatzki et al. |

FOREIGN PATENT DOCUMENTS

| | | |
|---|---|---|
| DE | 19507894 A1 | 9/1996 |
| DE | 10237267 A1 | 10/2003 |
| DE | 60012937 T2 | 9/2005 |
| DE | 102009051441 A1 | 5/2011 |
| DE | 102010049894 A1 | 5/2012 |
| DE | 102013000770 A1 | 7/2014 |
| WO | 2012055401 A1 | 5/2012 |

\* cited by examiner

ANKLE BRACE

TECHNICAL FIELD

The invention relates to an ankle sleeve for a prosthetic device comprising a prosthetic foot and a below-knee part, said ankle sleeve being provided to bridge a free space between the prosthetic foot and the below-knee part and having a main body which is made from a flexible material and which comprises a cavity for receiving the prosthetic device. The ankle sleeve serves both as a cosmetic arrangement and also as a protective sheath for prosthesis components.

BACKGROUND

Prosthetic devices for lower extremities in principle have a prosthetic foot and a below-knee part, which are connected to each other. The prosthetic feet can be fastened on the below-knee part in different ways; in addition to rigid fastening, a hinged arrangement of the prosthetic foot on the below-knee part is increasingly being used. Prosthetic devices, in particular those with a prosthetic knee joint, often have damping mechanisms, drives and controls, which are usually arranged in the below-knee part. The below-knee part thus assumes functions that go beyond that of simply connecting the prosthetic foot to a prosthetic knee joint.

The prosthetic feet have developed from a rigid imitation of the foot to complex structural parts which can have controllable damping and components for converting mechanical energy to electrical energy. An articulated connection in the ankle area is also possible.

Prosthesis covers are used in order to ensure a cosmetically appealing design of the prosthetic device. In the design of a below-knee part as a below-knee tube, a plastic foam body is cut to the shape of a lower leg and modeled and placed around the below-knee tube.

It is also known from the prior art to use a stocking-like cover in order to approximate the appearance and look of a prosthetic device to that of a natural limb. A stocking-like cover of this kind is known from DE 2130168 A1. This stocking-like cover avoids the wear to which stockings are subject; it does this by having no direct contact with the surfaces of the prosthesis.

DE 10 2009 051 441 A1 relates to an artificial limb casing having an insertion opening for inserting an artificial limb, wherein a joint area is formed on the casing, into which joint area an end area is integrally connected into which a prosthetic foot can be inserted. There is a lower Shore hardness in the joint area than in the end area. An artificial limb casing of this kind has to be placed around the artificial limb, in this case a prosthetic foot, which is quite awkward to do. In addition, there are prosthetic feet which have a shape approximated to the natural foot and do not require any further covering.

SUMMARY

The object of the present invention is to make available an ankle sleeve with which a free space between a prosthetic foot and a below-knee part can be bridged, the aim being to permit versatile use for different combinations of below-knee part and prosthetic foot.

According to the invention, this object is achieved by an ankle sleeve having the features of the main claim. Advantageous embodiments and developments of the invention are disclosed in the dependent claims, the description and the figures.

In the ankle sleeve for a prosthetic device with a prosthetic foot and a thigh, for bridging a free space between the prosthetic foot and the thigh, with a main body which is made from a flexible material and which comprises a cavity for receiving the prosthetic device, provision is made that at least one reinforcement element is arranged on the main body in order to increase the inherent stability of the ankle sleeve. The ankle sleeve serves to bridge a free space or transition from the upper edge or the proximal end of the prosthetic foot and a below-knee part, for example a housing of a damping and controlling mechanism, or of another component simulating the volume of a natural lower leg and/or performing the function of a below-knee tube. For this purpose, the ankle sleeve has a main body which is made from a flexible material. In the fitted state, the main body forms a cavity in which the prosthetic device, mainly a part of the below-knee part, is arranged. The main body thus surrounds a distal portion of the below-knee part in the area of the transition to the prosthetic foot. A reinforcement element is arranged, for example adhesively bonded, welded, injected or integrally formed, on the main body or secured in some other way, in order, on the one hand, to generate an appearance corresponding to the natural ankle area or distal lower leg area, and, on the other hand, to provide a functional cover for the mechanical components of the prosthetic device. The reinforcement element ensures that the ankle sleeve has a sufficient dimensional stability during movement of the prosthetic device, without the mobility being too greatly restricted. Likewise, sufficient deformability is ensured by the flexible main body, such that a natural impression is again afforded. By means of the reinforcement element, it is possible to adapt the functionality of the ankle sleeve to the desired properties, namely that there is sufficient stability to prevent the sleeve from slipping down or slipping off, without losing the flexibility that is needed to avoid folding or collapsing of the sleeve, as would be the case upon buckling of a rigid material, for instance that of a rubber boot.

The reinforcement element in this case consists of a material that has a greater deformation resistance than the material of the main body, so that the desired dimensional stability and the desired deformation resistance can be achieved or increased specifically at those points at which the reinforcement element is arranged. It is likewise possible, by means of the reinforcement element, to provide an improved mechanical protective effect at particularly sensitive points at the transition between the prosthetic foot and the below-knee part.

Alternatively, the reinforcement element can be in the form of a thickening of the base material. In this case, the base material and the reinforcement element are made of the same material. Preferably, the ankle sleeve is in this case injected or cast.

The main body can be produced from a textile and/or a foam or comprise a textile and/or a foam and further materials where necessary. Textiles and foams have the advantage of being easy to produce and process and of being lightweight while having sufficient flexibility and deformability. The textiles may be formed as woven or knitted fabrics and as knitted spacer fabrics; as foams, both open-cell and closed-cell foams are envisaged. The main body can have a coating, which increases or establishes the water impermeability of the ankle sleeve.

Alternatively, the main body of the bridging element can also be produced from an elastomer, for example from a silicone or TPE or a softened thermoplastic, for example a soft PVC.

For securing the ankle sleeve with a form fit on the prosthetic foot, fastening elements can be arranged on the main body or on the reinforcement element, such that a relative movement between the ankle sleeve and the prosthetic foot cannot take place during the routine use of the prosthetic device. It is thus possible to form or orient the ankle sleeve so that it is flush, or virtually flush, with the proximal end of the prosthetic foot. The fastening elements for the form-fitting securement also have the effect that the contour of the ankle sleeve adapts itself to the contour of the prosthetic foot, such that it is possible to combine different forms of prosthetic feet with one and the same ankle sleeve.

In a development of the invention, provision is made that the reinforcement element is formed as a frame which surrounds the main body. The frame can be arranged peripherally about the entire circumference of the main body, such that there is sufficient dimensional stability for mounting the ankle sleeve, for example on the prosthetic foot or on the below-knee part. The hollow space that is surrounded by the main body is defined by the frame, such that the main body itself can be formed from a flexurally slack material which is kept in the desired form by the reinforcement element.

At least one hinge mechanism can be arranged in the reinforcement element in order to facilitate flexion about an ankle joint. This hinge mechanism facilitates the relative movement between the prosthetic foot and the below-knee part and prevents noises from being produced during flexing due to folding of the ankle sleeve. Furthermore, the extraction forces that occur during flexion about an ankle joint, whether plantar flexion or dorsiflexion, are reduced. Reducing the extraction forces ensures that the ankle sleeve remains in the intended position relative to the prosthetic foot or the below-knee part.

The ankle sleeve is advantageously symmetrically formed, the symmetry preferably being in relation to the sagittal plane, such that one sleeve is suitable for use both on a left-hand prosthetic device and on a right-hand prosthetic device.

The reinforcement element can form the distal end of the ankle sleeve, wherein at least parts of the reinforcement element form the distal end. As a result, it is possible that particularly fastening elements, which of course must have a greater strength than the flexurally slack or flexible material of the main body, can be produced and formed on more easily. In the case of a separate configuration of the fastening elements, it is possible by the arrangement at the distal end of the ankle sleeve to achieve an easy assignment of the fastening elements both to the ankle sleeve and to the prosthetic foot. The fastening elements can in this case be secured in a form-fitting manner on the ankle sleeve at a form-fitting element, the form-fitting element being formed on or fastened to the reinforcement element.

A friction-reducing coating can be arranged on the inner face, in particular in the proximal area of the main body, and similarly friction-reducing elements can be arranged on the inner face of the main body, for example adhesively bonded, injected, welded on or fastened in some other way to the main body. A friction-reducing coating makes it possible to permit a relative movement between the ankle sleeve and the below-knee part without high extraction forces acting on the ankle sleeve, such that a fixed assignment between the distal end of the ankle sleeve and the proximal end of the prosthetic foot is maintained.

The reinforcement element can have a closed cross section, in order to further increase the dimensional stability. The form is generally oval or made to approximate an oval. The reinforcement element can extend over a relatively great range of height in the proximal-distal extent, it being possible for cutouts to be provided in the reinforcement element in the anterior and/or posterior orientation. These cutouts make it possible to allow a deformation of the material of the main body. For this purpose, provision is made that the reinforcement element is provided on the main body, such that the cutouts possibly provided in the reinforcement element are covered by the material of the main body. In the fitted state, the ankle sleeve is thus preferably closed, such that no moisture and/or dirt can penetrate.

As an alternative to a closed cross section of the reinforcement element, provision is made that the main body has an open cross section and the reinforcement element is also or only arranged along the opening and closes the cross section, that is to say receives and fixes the opposing edges of the blank of the main body and altogether provides a closed cross section for the ankle sleeve.

BRIEF DESCRIPTION OF THE DRAWINGS

Illustrative embodiments of the invention are explained in more detail below with reference to the attached figures, in which.

DETAILED DESCRIPTION

Figure 1:
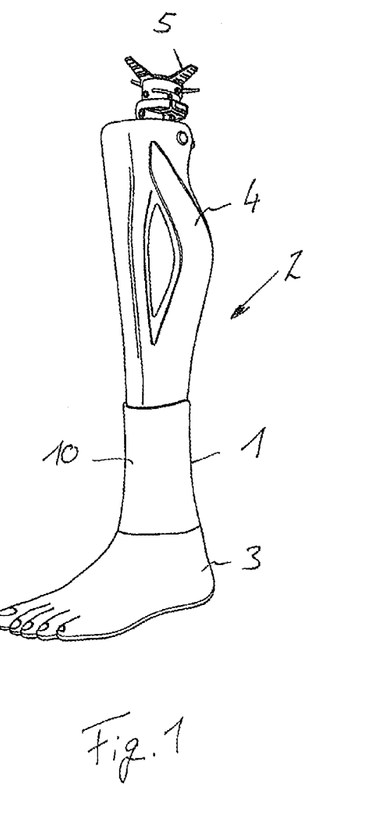
FIG. 1 shows a side view of a prosthetic device with an ankle sleeve.

FIG. 1 shows an overall view of a prosthetic device 2 having a prosthetic foot 3, a below-knee part 4 fastened on the proximal end of the prosthetic foot 3, and a fastening mechanism 5 arranged on the proximal end of the below-knee part 4. The fastening mechanism 5 serves to mount the prosthetic device 2 on a thigh socket (not shown). The fastening mechanism 5 is mounted in an articulated manner on the below-knee part 4 and is thus part of a prosthetic knee joint. Above the prosthetic foot 3, i.e. adjoining the proximal end of the prosthetic foot 3, an ankle sleeve 1 is arranged which has a main body 10. The ankle sleeve 1 bridges the transition area from the prosthetic foot 3 to the below-knee part 4 and extends along approximately one third of the length of the below-knee part 4. The ankle sleeve 1 completely surrounds the below-knee part 4 and is secured reversibly on the prosthetic foot 3 via form-fit elements (not shown).

Figure 2:
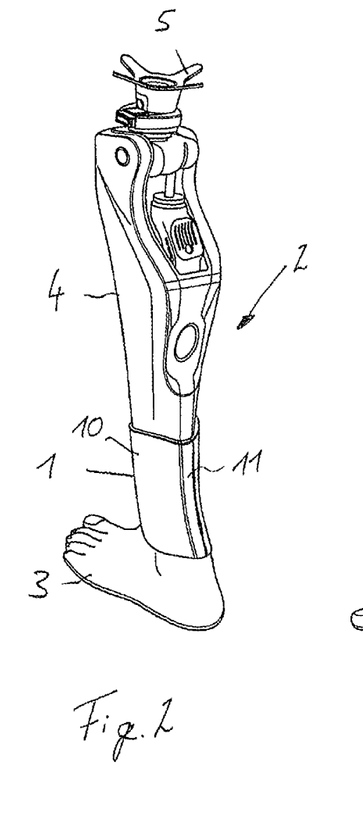
FIG. 2 shows a view of an ankle sleeve obliquely from behind.

In FIG. 2, the prosthetic device 2 with the ankle sleeve 1 is shown obliquely from behind. Damping mechanisms, control electronics and the prosthetic knee joint can be seen in the below-knee part 4. On the posterior face, the ankle sleeve 1 itself has a reinforcement element 11 arranged on the main body 10, which reinforcement element 11 is thus arranged on the posterior face of the prosthetic device 2, i.e. in the area of the calf, and extends substantially in the longitudinal direction of the below-knee part 4. The reinforcement element 11 serves, in the first instance, to ensure the stability of the ankle sleeve 1 in the longitudinal extent thereof and prevents the ankle sleeve 1 from slipping down, during use, from the below-knee part 4 in the direction of the prosthetic foot 3 and possibly forming folds. The reinforcement element 11 moreover serves to connect the mutually opposite ends of the main body 10 which, in the illustrative embodiment shown, is not designed as a circular or oval material blank with a closed cross section but instead as a flat blank with an open cross section, wherein the mutually opposite edges of the blank are connected to each other via the reinforcement element 11, such that a cavity is made available for receiving the prosthetic device 2, in particular the lower or distal part of the below-knee part 4.

Figure 3:
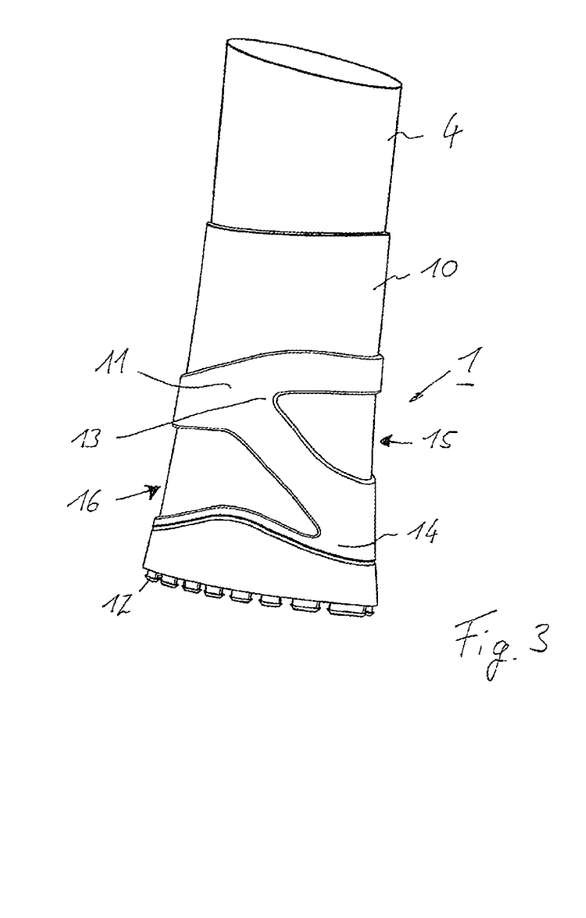
FIG. 3 shows a view of a variant of an ankle sleeve on its own.

FIG. 3 shows a variant of the ankle sleeve 1 arranged on a below-knee part 4. The prosthetic foot is not shown in FIG. 3. The ankle sleeve 1 has a main body made of a flexible material, in particular a textile, a foam or a combination of several flexible materials. In the illustrative embodiment shown, the main body 10 is hose-shaped and has a closed cross section. Arranged on the outside of the main body 10 there is a reinforcement element 11 in the form of a frame which, inter alia, forms a peripheral distal end of the ankle sleeve 1. Fastening elements permitting form-fit engagement on the prosthetic foot are provided at the distal end of the reinforcement element 11. In addition to the illustrated one-piece variant with integrally formed fastening elements 12, it is possible to secure separate fastening elements on the reinforcement element 11 in order then to bring these into engagement with form-fit elements on the prosthetic foot and there to secure the ankle sleeve 1 with form-fit engagement on the prosthetic foot.

At the distal end of the main body 10, the reinforcement element 11 is designed as a peripherally closed ring, from the posterior end of which, on the right in FIG. 3, a frame portion extends obliquely upward. The transition from the lower, annular end to the upwardly directed frame portion is designed as a hinge mechanism 14, such that a resilient movement of the anterior or front area of the reinforcement element 11 can take place downward or in the distal direction. For this purpose, an anterior recess 16 is provided in the reinforcement element 11, which recess 16 is filled by the material of the main body 10.

From the obliquely forwardly extending frame portion of the reinforcement element 11, an upper part extends, inclined slightly upward, obliquely rearward and upward, i.e. toward the proximal end of the ankle sleeve 1, and thus forms a bow which extends around the posterior part of the main body 10 above the posterior hinge 14. A second hinge element or a second hinge mechanism 13 is arranged and formed at the transition from the obliquely forwardly directed frame portion to the obliquely rearwardly directed frame portion, such that the obliquely rearwardly extending frame portion can be moved downward. Below the upper frame portion, a posterior recess 15 is formed, which is likewise closed by the material of the main body 10. If a plantar flexion of the prosthetic foot 3 is performed, then, analogously to a natural movement of a foot, the upper rearwardly directed frame portion moves about the hinge mechanism 13 causing a flexible deformation of the material of the main body 10 within the recess 15 by compression, while the flexible material of the main body 10 in the area of the anterior recess 16 is stretched and the forwardly extending frame part is moved upward. In the case of dorsiflexion, compression takes place in the area of the anterior recess 16 and stretching takes place in the area of the posterior recess 15. In addition to a one-piece design of the reinforcement element 11, provision is made that it has a multi-part or modular configuration, such that, for example, the lower annular frame is connected to the upper frame portions, if appropriate connected in an articulated manner via a hinge or several hinges.

Figure 4:
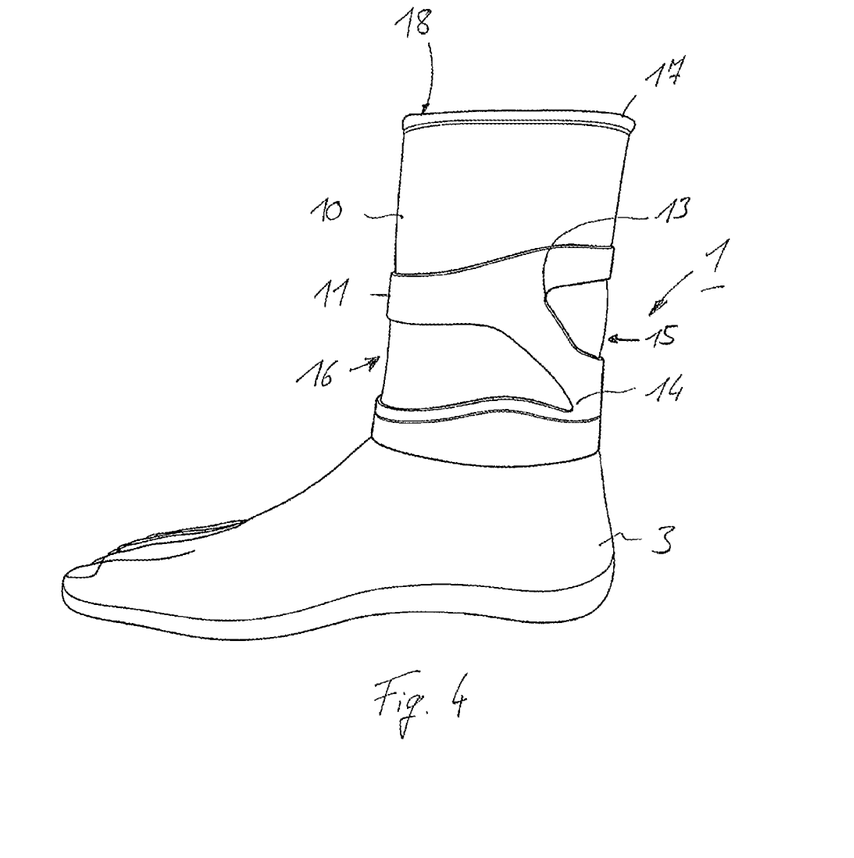
FIG. 4 shows a side view according to FIG. 3.

FIG. 4 shows a side view of the embodiment according to FIG. 3 in a state when fitted on the prosthetic foot 3. The fastening elements 12 are inserted into recesses (not shown) in the upper edge of the prosthetic foot end and make it possible to mount the ankle sleeve 1 flush on the prosthetic foot 3. In addition to a fastening action secure against a withdrawal movement, i.e. away from the prosthetic foot 3, the fastening elements 12 also allow the ankle sleeve 1 to adapt to the contour of the respective prosthetic foot 3 since, in addition to the main body 10, the reinforcement element also has a flexibility and elasticity, such that different prosthetic feet 3 can be supplied with just one ankle sleeve 1. It will be seen in FIG. 4 that the reinforcement element 11 holds the main body 10 in the desired shape, such that the main body 10 encloses a cavity which protrudes beyond the proximal edge of the reinforcement element 11. A friction-reducing coating 18 can be arranged on the inner face 18 at the proximal edge 17 of the main body 10 in order to facilitate a relative movement between the below-knee part 4 (not shown) and the material of the main body 10. FIG. 4 also shows the hinges 13, 14 arranged in different directions with the hinge 13 open in a rearward direction and the hinge 14 open in a forward direction. Furthermore, FIG. 5 shows a separate set of hinges 13, 14 on each of the medial and lateral sides of the main body 10.

Figure 5:
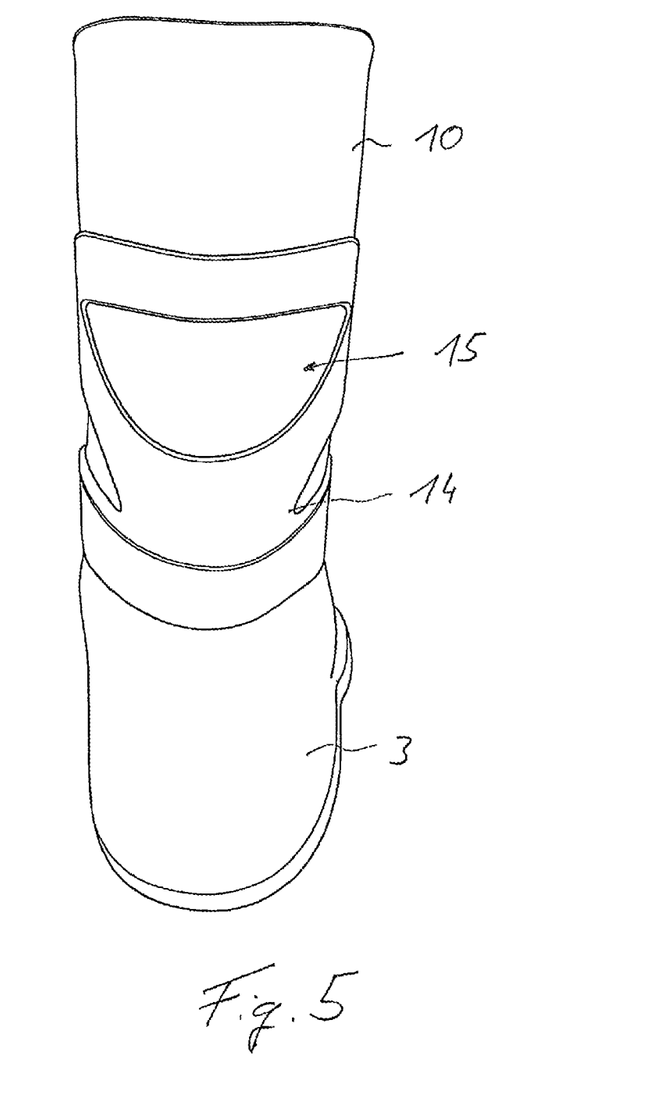
FIG. 5 shows a rear view according to FIG. 3.

FIG. 5 shows a rear view of the embodiment according to FIG. 4, depicting the prosthetic foot 3 with the surrounding reinforcement element 11 flush about the circumference. In the posterior area, i.e. in the area of the Achilles tendon, the hinge mechanism 14, which is formed by the recess 16, is formed above the distal ring of the reinforcement element 11. The hinge mechanism 14 has the effect that the parts or portion of the reinforcement element 11 extending upward, i.e. toward the proximal end of the ankle sleeve 10, can be slightly flexed; in the posterior hinge 14 this means that the portions of the reinforcement element 11 adjacent at the top can move forward and downward, i.e. in the direction of the prosthetic foot, in dorsiflexion. In plantar flexion, the upper or anterior hinge 13 assumes this function and allows the posterior, proximal portion of the reinforcement element 11 to move in the distal direction, such that the posterior recess 15 is made smaller and the material of the main body 10 is compressed.

Figure 6:
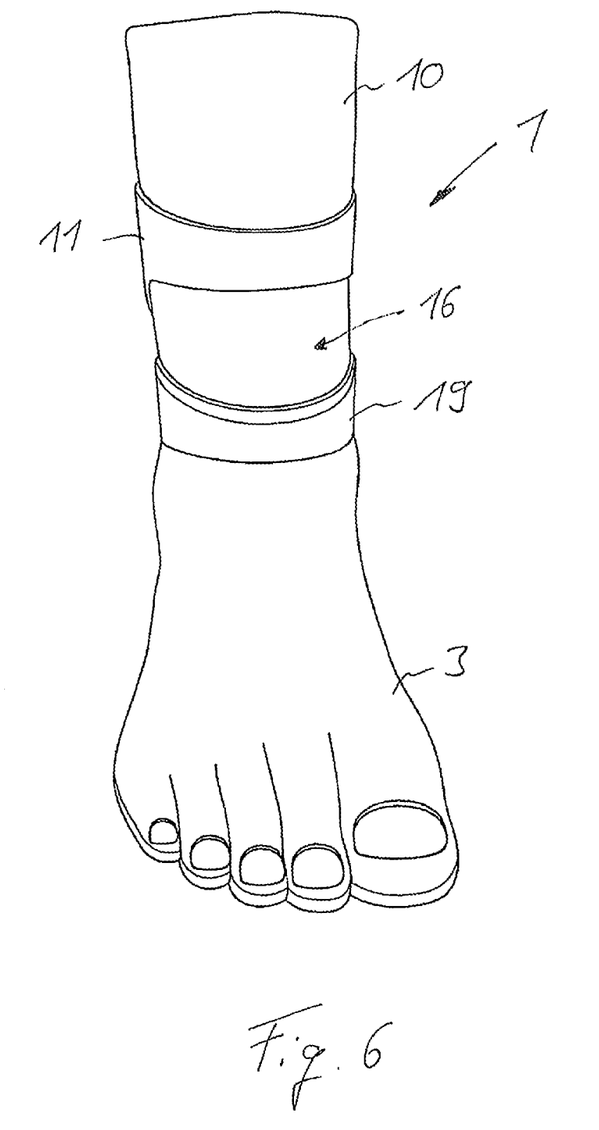
FIG. 6 shows a front view according to FIG. 3.

FIG. 6 shows a front view of the embodiment according to FIGS. 4 and 5. It will be seen that the reinforcement element 11 has, in the anterior area, a recess 16 which is filled by the main body 10. In the distal area, the reinforcement element 11 has a peripheral ring 19 with a closed cross section. The reinforcement element 11 serves to increase the inherent stability of the ankle sleeve 1 and at the same time constitutes a mechanical protection against environmental influences for the ankle joint or for the electronics arranged in the below-knee part 4. The reinforcement element 11 can be welded, adhesively bonded, sewn or injected onto the material of the main body 10. In the illustrative embodiment shown, the reinforcement element 11 is arranged on the outer face of the main body 10, although it is also possible that it is arranged on the inner face of the main body or encloses the main body 10, i.e. is arranged on the outer face and inner face of the main body 10.

Figure 7:
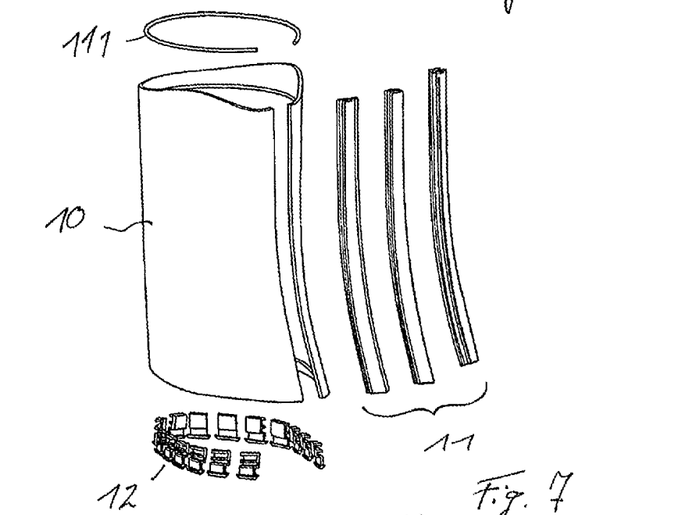
FIG. 7 shows a view of a variant in its individual parts.

A variant of the invention is shown in FIG. 7, which shows an embodiment according to FIG. 1 in its individual parts. The main body 10 is designed as a substantially flat blank and is shaped such that the mutually opposite edges can be joined together in order to form a hose-like hollow body. In the illustrative embodiment shown, the reinforcement element 11 is designed in several parts and has two side rails that are fastened on the main body 10. These side rails are connected to each other with a form fit via a central rail. For this purpose, the central rail has recesses into which form-fit elements of the side rails engage. In order to achieve a peripheral stability, a further reinforcement element 111 is provided which, in the illustrative embodiment shown, is arranged at the proximal end of the main body 10. The reinforcement element 111 can be designed as a spring wire or plastic clasp.

At the distal end of the main body 10, separate fastening elements 12 are provided which are secured there with a form-fit action and have projections with which the fastening elements 12 and thus also the main body 10 with the reinforcement element 11 can be secured on the prosthetic foot.

Figure 8:
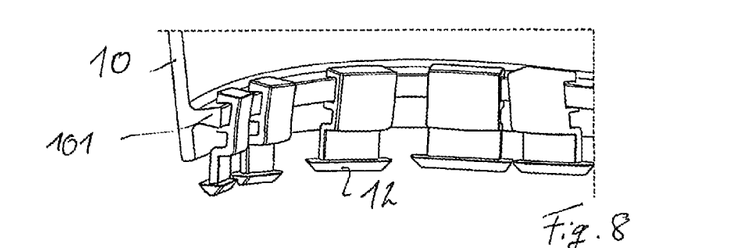
FIG. 8 shows a detailed view of the variant according to FIG. 7.

FIG. 8 shows an enlarged detailed view of the distal end of the main body 10 on which a peripheral projection 101 is arranged which, for example, can be injected thereon or formed thereon. The projection 101 has a V-shaped cross section which tapers toward the outer wall of the main body 10. The fastening elements 12 have a dovetail-shaped recess, such that they can engage with a form fit in the projection 101. At the distal end of the fastening elements 12, arrow-shaped projections are formed in order to permit form-fit locking by engagement with corresponding recesses in the prosthetic foot. The fastening elements 12 are secured reversibly and displaceably on the main body 10, such that different numbers of fastening elements can be secured on the respective blanks. By virtue of the displaceability of the fastening elements 12 on the main body 10, it is possible to operate different prosthetic foot sizes with a blank of the main body 10 or, if appropriate with slight modification, to permit an adaptation. The larger the prosthetic feet, the greater the distance between the individual recesses for the respective fastening elements, such that an adaptation cannot take place without displaceable fastening elements 12.

Figure 9:
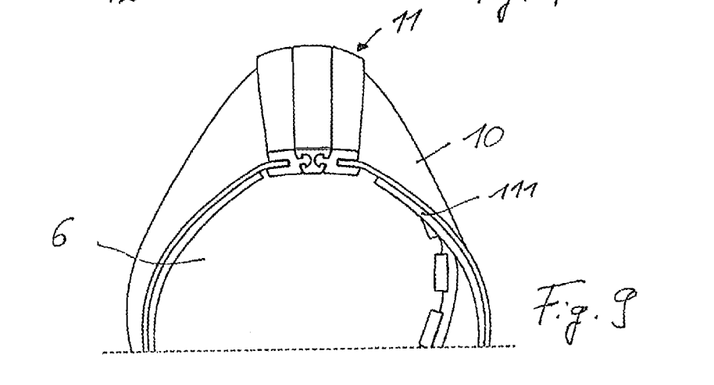
FIG. 9 shows a partial sectional view of the variant according to FIG. 7 in an oblique view from above.

FIG. 9 shows the assembled ankle sleeve 1 with the main body 10, the reinforcement element 111 acting in the circumferential direction, and the reinforcement element 11 acting in the longitudinal extent with the two outer rails and the central rail secured thereon with a form fit. By means of the reinforcement element 11, a closed cavity 6 is formed which receives the respective component of the prosthetic device.

Figure 10:
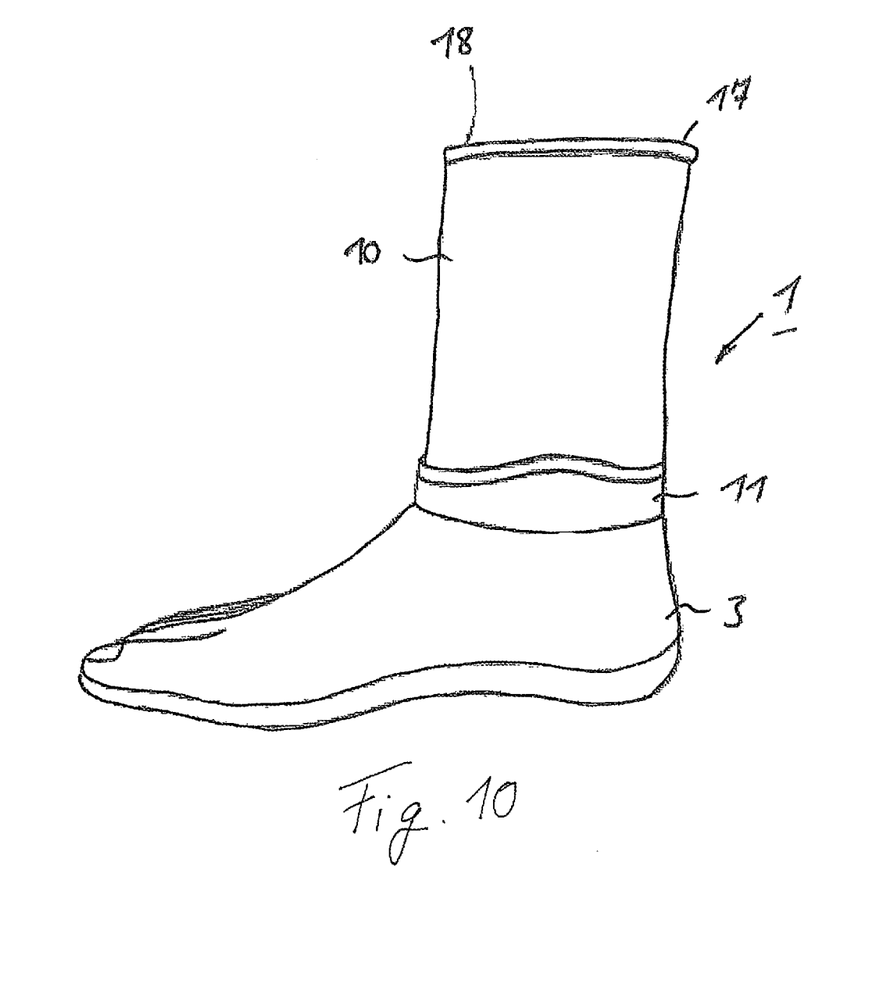
FIG. 10 shows a variant in a side view.

FIG. 10 shows a further variant of the invention. The variant corresponds substantially to the embodiment according to FIG. 4. However, the reinforcement element 11 is arranged or formed in the distal area of the main body 10, for example by means of a separate layer of material being injected on, integrally formed or adhesively bonded, or by thickening and, if appropriate, changing the property of the basic material in order to achieve increased dimensional stability in the distal area of the ankle sleeve 1. The proximal portion of the main body 10, i.e. the portion arranged in the proximal direction relative to the reinforcement element 11, has a sufficient inherent stability in order to bridge the space between the prosthetic foot 3 and the below-knee part 4 (not shown). In the case of thickening, the change of property of the material of the main body 10 can take place by compression or thermal treatment. In principle, in the other embodiments, it is also possible, in addition to a separate design of the reinforcement element 11, to configure the latter as one or more thickenings.

The invention claimed is:

1. An ankle sleeve for bridging a free space between a prosthetic foot and a below-knee part, the ankle sleeve comprising:
   a proximal end having a proximal opening;
   a distal end having a distal opening;
   a main body comprising:
      a flexible material;
      a cavity for receiving portions of the prosthetic foot and the below-knee part;
   a reinforcement element arranged on the main body to increase an inherent stability of the ankle sleeve, the reinforcing element comprising at least first and second hinges arranged in different directions;
   a plurality of fastening elements positioned along a distal edge to secure the ankle sleeve to the prosthetic foot.

2. The ankle sleeve as claimed in claim 1, wherein the at least one reinforcement element is made from a material with a greater deformation resistance than the flexible material of the main body.

3. The ankle sleeve as claimed in claim 1, wherein the flexible material of main body is produced from one of a textile and/or a foam.

4. The ankle sleeve as claimed in claim 1, wherein the plurality of fastening elements secure the ankle sleeve on the prosthetic foot with a form-fit engagement.

5. The ankle sleeve as claimed in claim 1, wherein the at least one reinforcement element is a frame surrounding the main body.

6. The ankle sleeve as claimed in claim 1, wherein at least one hinge mechanism for facilitating a flexion motion about a prosthetic ankle joint is arranged in the at least one reinforcement element.

7. The ankle sleeve as claimed in claim 1, wherein the ankle sleeve has medial-lateral symmetry.

8. The ankle sleeve as claimed in claim 1, wherein the at least one reinforcement element forms a distal end of the ankle sleeve.

9. The ankle sleeve as claimed in claim 1, wherein a friction-reducing coating is arranged on a proximal inner face of the main body.

10. The ankle sleeve as claimed in claim 1, wherein the at least one reinforcement element has a closed cross section with cutouts oriented in an anterior direction and/or a posterior direction.

11. The ankle sleeve as claimed in claim 1, wherein the main body has an open cross section, and the at least one reinforcement element closes the cross section.

12. An ankle sleeve for bridging a free space between a prosthetic foot and a below-knee part, the ankle sleeve comprising:
   a proximal end having a proximal opening;
   a distal end having a distal opening;
   a main body, the main body comprising a flexible material;
   a cavity formed within the main body, the cavity configured to receive portions of the prosthetic foot and the below-knee part;
   at least one reinforcement element arranged on the main body, the reinforcement element providing an increased stability of the ankle sleeve and comprising at least first and second hinges arranged in different directions;

the cavity housing at least a damping and control mechanism of the below-knee part;
a plurality of fastening elements positioned along a distal edge to secure the ankle sleeve to the prosthetic foot.

13. The ankle sleeve of claim 12, wherein the at least one reinforcement element comprises a closed cross section.

14. The ankle sleeve of claim 12, wherein the at least one reinforcement element comprises:
a frame, the frame surrounding the main body;
an anterior recess formed in an anterior portion of the frame.

15. The ankle sleeve of claim 14, further comprising:
an annular end of the at least one reinforcement member, the annular end at a distal end of the main body;
an upwardly directed frame portion of the at least one reinforcement member, the upwardly directed frame portion extending obliquely upward from the posterior end of the main body towards the anterior portion of the main body;
the anterior recess separating the annular end and the upwardly directed frame portion at the anterior portion of the main body.

16. The ankle sleeve of claim 15, wherein the first hinge transitioning the annular end to the upwardly directed frame portion.

17. The ankle sleeve of claim 16, further comprising:
an upper part, the upper part extending slightly upward and obliquely rearward and upward towards a proximal end of the main body;
the second hinge mechanism formed at a transition between the upwardly directed frame portion and the upper part.

18. The ankle sleeve of claim 12, wherein the plurality of fastening elements secure the ankle sleeve to the prosthetic device with form-fit engagement.

19. The ankle sleeve of claim 12, further comprising:
a second reinforcement element, the second reinforcement element arranged at a proximal end of the main body, the second reinforcement element providing peripheral stability.

20. A prosthetic device, comprising:
a prosthetic foot;
a below the knee part, the below the knee part fastened on a proximal end of the prosthetic foot;
an ankle sleeve coupling the prosthetic foot and the below the knee part, the ankle sleeve comprising:
a proximal end having a proximal opening;
a distal end having a distal opening;
a main body, the main body comprising a flexible material;
a cavity formed within the main body, the cavity receiving portions of the prosthetic foot and the below the knee part;
at least one reinforcement element arranged on the main body, the at least one reinforcement element providing an increased stability of the ankle sleeve and comprising at least first and second hinges arranged in different directions;
the cavity housing at least a damping and control mechanism of the below the knee part;
a plurality of fastening elements positioned along a distal edge to secure the ankle sleeve to the prosthetic foot.

* * * * *